US010835730B2

(12) United States Patent
Chelak et al.

(10) Patent No.: US 10,835,730 B2
(45) Date of Patent: Nov. 17, 2020

(54) SAMPLING PORT FOR HEMODYNAMIC MONITORING SYSTEMS

(71) Applicant: NP Medical Inc., Clinton, MA (US)

(72) Inventors: Todd Chelak, Westborough, MA (US); Nicholas Illsley, Clinton, MA (US); Nicholas Dennis, Sterling, MA (US)

(73) Assignee: NP MEDICAL INC., Clinton, MA (US)

( * ) Notice: Subject to any disclaimer, the term of this patent is extended or adjusted under 35 U.S.C. 154(b) by 353 days.

(21) Appl. No.: 15/907,481

(22) Filed: Feb. 28, 2018

(65) Prior Publication Data

US 2018/0185627 A1 Jul. 5, 2018

Related U.S. Application Data

(63) Continuation-in-part of application No. 15/389,977, filed on Dec. 23, 2016, now Pat. No. 10,368,789.

(51) Int. Cl.
*A61M 39/06* (2006.01)
*A61B 5/0215* (2006.01)
(Continued)

(52) U.S. Cl.
CPC ........... *A61M 39/06* (2013.01); *A61B 5/0215* (2013.01); *A61B 5/02141* (2013.01);
(Continued)

(58) Field of Classification Search
CPC ........... A61B 5/150221; A61B 5/0215; A61B 5/150992; A61M 39/04; A61M 39/06;
(Continued)

(56) References Cited

U.S. PATENT DOCUMENTS 4,936,542 A 6/1990 Beard
5,098,405 A 3/1992 Peterson et al.
(Continued)

FOREIGN PATENT DOCUMENTS

EP 0 247 425 A2 12/1987
EP 1 234 596 A1 8/2002
(Continued)

OTHER PUBLICATIONS

Internation Search Report and Written Opinion for PCT/US2019/019524 dated Jun. 11, 2019, pp. 1-12.
(Continued)

*Primary Examiner* — Jason E Flick
*Assistant Examiner* — Tasnim Mehjabin Ahmed
(74) *Attorney, Agent, or Firm* — McCarter & English, LLP; Jonathan C. Lovely

(57) ABSTRACT

A medical valve has a housing with an inlet housing and an outlet housing. The interior of the inlet housing and/or the outlet housing has a contact surface. A resilient element sits within the housing and controls fluid flow through the inlet. The resilient element has a proximal portion with a normally closed aperture configured to open when actuated by a medical device. The resilient element also has a distal portion adjacent to the outlet, and a central portion between the proximal portion and the distal portion. The central portion has a wall that defines a fluid chamber in the open mode and in the closed mode. The wall has at least one projection extending radially outward. The projection maintains compressive contact with the contact surface of the housing and applies an inwardly compressive force on the resilient element, increasing the wall stiffness.

21 Claims, 13 Drawing Sheets

(51) Int. Cl.
*A61B 5/021* (2006.01)
*A61B 5/00* (2006.01)
*A61M 25/00* (2006.01)
*A61M 39/26* (2006.01)
*A61M 39/04* (2006.01)

(52) U.S. Cl.
CPC .......... *A61B 5/6848* (2013.01); *A61B 5/6866* (2013.01); *A61B 5/742* (2013.01); *A61B 2562/0247* (2013.01); *A61M 39/045* (2013.01); *A61M 39/26* (2013.01); *A61M 2025/0003* (2013.01); *A61M 2039/062* (2013.01); *A61M 2039/0633* (2013.01); *A61M 2039/0673* (2013.01)

(58) Field of Classification Search
CPC .... A61M 2039/0633; A61M 2039/064; A61M 2039/0646; A61M 2039/066; A61M 2039/0666; A61M 2039/027; A61M 2039/0673
See application file for complete search history.

(56) References Cited

U.S. PATENT DOCUMENTS

| | | | |
|---|---|---|---|
| 5,203,771 | A | 4/1993 | Melker et al. |
| 5,221,271 | A | 6/1993 | Nicholson et al. |
| 5,354,275 | A | 10/1994 | Behnke et al. |
| 5,360,413 | A | 11/1994 | Leason et al. |
| 5,417,673 | A | 5/1995 | Gordon |
| 6,089,541 | A | 7/2000 | Weinheimer et al. |
| RE37,357 | E | 9/2001 | Lynn |
| 7,314,061 | B2 | 1/2008 | Peppel |
| 7,314,452 | B2 | 1/2008 | Madonia |
| 7,556,060 | B2 | 7/2009 | Guala |
| 7,984,730 | B2 | 7/2011 | Ziv et al. |
| 8,708,976 | B1 | 4/2014 | Yeh et al. |
| 9,079,005 | B2 | 7/2015 | Chelak et al. |
| 9,192,753 | B2 | 11/2015 | Lopez et al. |
| 9,604,047 | B2 | 3/2017 | Newton et al. |
| 2005/0261637 | A1 | 11/2005 | Miller |
| 2006/0213563 | A1 | 9/2006 | Peppel |
| 2006/0217671 | A1 | 9/2006 | Peppel |
| 2007/0260195 | A1 | 11/2007 | Bartholomew et al. |
| 2011/0282302 | A1* | 11/2011 | Lopez .................. A61M 39/16 604/247 |
| 2011/0308651 | A1 | 12/2011 | Ziv et al. |
| 2014/0276215 | A1* | 9/2014 | Nelson ................ A61M 39/223 600/573 |
| 2015/0112271 | A1 | 4/2015 | Chelak et al. |

FOREIGN PATENT DOCUMENTS

| | | |
|---|---|---|
| WO | WO 2006/052655 | 5/2006 |
| WO | WO 2008/101025 A1 | 8/2008 |
| WO | 2014/123678 A1 | 8/2014 |
| WO | WO 2015/100135 | 7/2015 |

OTHER PUBLICATIONS

International Searching Authority, International Search Report—International Application No. PCT/US2014/058234, dated Dec. 16, 2014 together with the Written Opinion of the International Searching Authority, 10 pages.

International Searching Authority, International Search Report—International Application No. PCT/US2017/065944, dated Apr. 9, 2018 together with the Written Opinion of the International Searching Authority, 12 pages.

\* cited by examiner

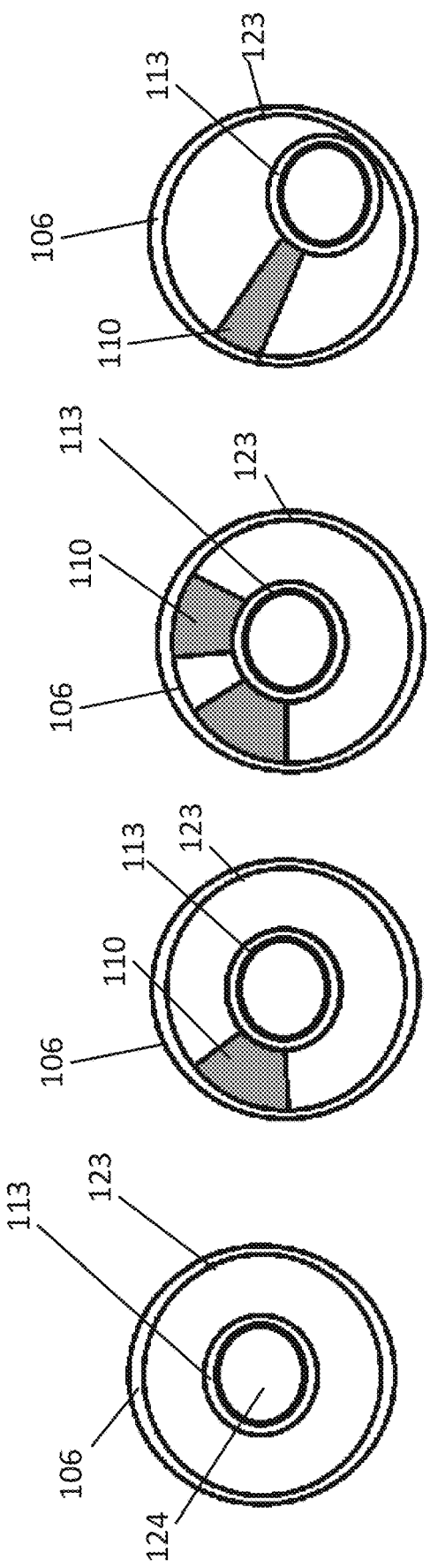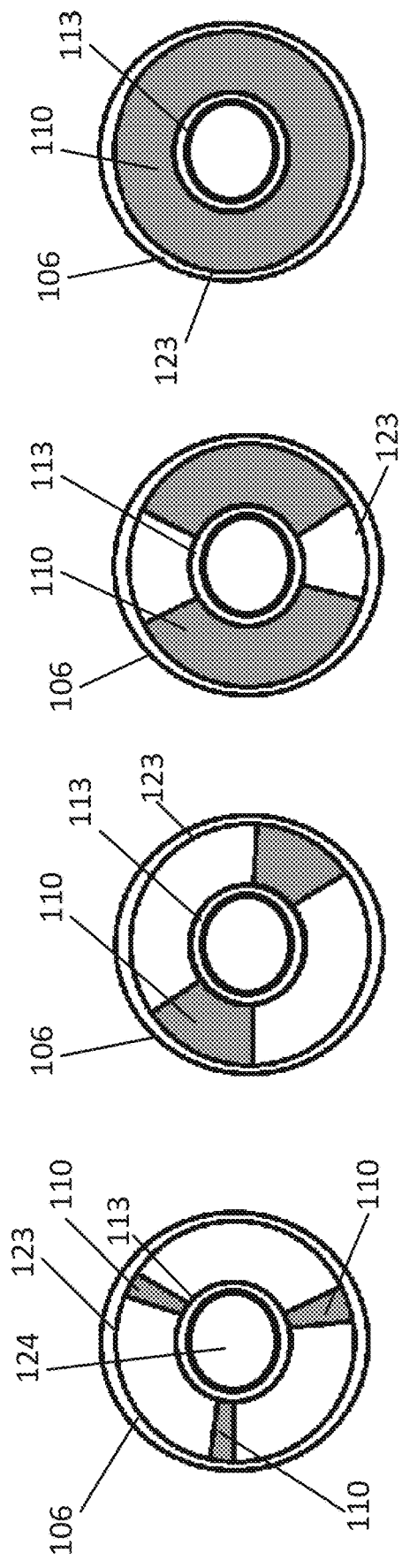

SAMPLING PORT FOR HEMODYNAMIC MONITORING SYSTEMS

PRIORITY

This patent application is a continuation-in-part of U.S. patent application Ser. No. 15/389,977, filed Dec. 23, 2016, entitled, "MEDICAL PORT WITH CONSTRAINING BIASING ELEMENT," and naming Todd Chelak, Ian Kimball, Ray Adams, and Jeffrey Ransden as inventors, the disclosure of which is incorporated herein, in its entirety, by reference.

FIELD OF THE INVENTION

Illustrative embodiments of the invention generally relate to fluid delivery and medical porting devices and, more particularly, the various embodiments of the invention relate to sample ports within arterial or venous fluid transfer and pressure monitoring sets.

BACKGROUND OF THE INVENTION

Many patient fluid transfer applications require a medical practitioner to take a sample of blood or fluid from the patient through an indwelling catheter. To that end, the practitioner typically uses a fluid transfer set having a sample port that allows the medical practitioner to draw a sample of the blood or fluid from the patient's indwelling catheter.

In some critical care applications, the medical practitioner may regularly monitor the patient's arterial or venous blood pressure through the fluid transfer set. In such applications, the fluid transfer set can include a pressure transducer that connects to a display that graphically shows a read-out of the arterial or venous blood pressure. Undesirably, the sampling ports of prior art fluid transfer sets can negatively interfere with the pressure transducer, causing erroneous blood pressure read-outs.

SUMMARY OF VARIOUS EMBODIMENTS

In accordance with one embodiment of the invention, a medical valve has an open mode that permits fluid flow, and a closed mode that prevents fluid flow. The valve is configured to be used in-line and in fluid communication with a pressure transducer. Accordingly the valve has a housing with an inlet and an outlet. The housing has an interior contact surface at and/or between the inlet and/or the outlet. A resilient valve element sits within the housing interior and is configured to control fluid flow through the inlet. The resilient valve element has a body including a proximal portion that forms a normally closed aperture configured to open when actuated by a medical device. The resilient valve element also has a distal portion adjacent to the outlet, and a central portion between the proximal portion and the distal portion. The central portion of the resilient valve element has a wall with an interior surface that defines a fluid chamber in the open mode and in the closed mode. The wall has at least one gland projection extending radially outwardly. The gland projection and the contact surface of the housing are configured to maintain compressive contact to apply a radially inwardly compressive force on the resilient valve element when the valve is in the closed mode, thereby increasing the stiffness of the wall to reduce waveform distortion, as measured by the pressure transducer. The at least one gland projection is distal of the normally closed aperture.

Among other directions, the gland projections may extend radially on the wall. To that end, a plurality of gland projections on the wall may be spaced apart in a circular array around the central axis to form an interrupted ring. The interrupted ring may form interstices between the gland projections. The wall may have ribs, on an inner surface of the wall, that correspond to the interstices.

The at least one gland projection may form a ring around the wall. In some embodiments, a plurality of gland projections may form a non-uniform ring around the wall. In some embodiments, at least 180 degrees of a circumference of the gland has gland projections. In some embodiments, the sum of the contact surface area of the at least one gland projection may be at least 0.01 inches squared. Furthermore, the at least one projection may be configured to diametrically compress the gland wall at least 0.003 inches when the valve is in the closed mode.

Additionally, or alternatively, a plurality of gland projections may be disposed on the wall and the gland projections may be spaced apart with respect to the central axis of the resilient valve element. In some embodiments, at least a portion of the gland projections are concyclic. Furthermore, a plurality of gland projections may form a plurality of rings spaced apart with respect to the central axis of the resilient valve element.

The gland projection may contact the contact surface of the inlet and/or the outlet when the valve is in the open mode. The at least one gland projection may form a slip plane with the resilient valve element. The gland projection may extend along substantially the entire length of the central portion.

Furthermore, the inlet and/or the outlet may have at least one housing projection extending towards the central axis of the resilient valve element. The inwardly facing projection may be configured to maintain compressive contact with the gland wall and to apply an inwardly compressive force on the resilient valve element when the valve is in the closed mode. The compressive contact may stiffen the gland wall and significantly reduce waveform distortion. In some embodiments, the compressive contact compresses a thickness of the gland wall by at least 1% when the valve is in the closed mode. Some embodiments may include a plurality of gland projections that form an interstice between a pair of spaced apart gland projections. The housing projections may be configured to contact the interstice. The gland projections may be spaced apart radially around the central axis. Additionally, or alternatively, the gland projections may be spaced apart along the central axis.

In accordance with yet another embodiment, a method reduces and/or removes artifacts from a pressure-waveform reading taken from a pressure transducer that is in-line with a medical valve. The medical valve has an open mode that permits fluid flow, and a closed mode that prevents fluid flow. The method provides a pressure transducer in-line and in fluid communication with a valve including a housing having an inlet and an outlet. The housing has an interior contact surface at and/or between the inlet and/or the outlet. The valve also has a resilient valve element within the housing interior that is configured to control fluid flow through the inlet. To that end, the resilient valve element has a body with a proximal portion having a normally closed aperture configured to open when actuated by a medical device, a distal portion adjacent to the outlet, and a central portion between the proximal portion and the distal portion.

The central portion has a wall with an interior surface that defines a fluid chamber in the open mode and in the closed mode. The wall also has at least one gland projection extending radially outwardly. When the valve is in the closed mode, the method compressively contacts the gland projection with the contact surface of the housing so as to apply a radially inwardly compressive force on the resilient valve element, thereby increasing the stiffness of the wall. The method then displays the pressure waveform reading.

In accordance with another embodiment, a gland is configured to sit within a valve housing interior to control fluid flow through the valve. A longitudinal axis runs through the length of the gland. The gland has a proximal portion with a normally closed aperture that leads to a lumen surrounded by a gland wall. The gland also has at least one compression tab formed on an outer surface of the gland wall. The at least one compression tab is configured to stiffen the gland wall in response to contact from an inner surface of the valve housing. To that end, each compression tab has a contact surface area.

In some embodiments at least two compression tabs are connected by at least one compression tab strip. Furthermore, a plurality of the compression tabs connected by the compression tab strips may form a non-uniform ring on the gland wall. The total contact surface area of each compression tab may be at least 0.01 inches squared and/or the compression tab may extend 0.05 inches from the outer surface of the gland wall.

In accordance with another embodiment, a medical valve has an open mode that permits fluid flow, and a closed mode that prevents fluid flow. The valve has a housing with an inlet and an outlet. The housing has an interior contact surface at and/or between the inlet and/or the outlet. A resilient valve element sits within the housing interior and is configured to control fluid flow through the inlet. The resilient valve element has a body including a proximal portion that forms a normally closed aperture configured to open when actuated by a medical device. The resilient valve element also has a distal portion adjacent to the outlet, and a central portion between the proximal portion and the distal portion. The central portion of the resilient valve element has a wall with an interior surface that defines a fluid chamber in the open mode and in the closed mode. Means for compression extend radially outwardly from at least one or both of the central portion and the distal portion. The compression means and the contact surface of the housing are configured to maintain compressive contact to apply a radially inwardly compressive force on the resilient valve element when the valve is in the closed mode, thereby increasing the stiffness of the wall. The compression means is distal of the normally closed aperture.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 4A schematically shows a cross-sectional view of a gland of the prior art that is uncompressed by the inner diameter of the housing.

FIGS. 4B-4H schematically show cross-sectional views of various embodiments of the gland within the housing, in accordance with illustrative embodiments of the invention.

DESCRIPTION OF ILLUSTRATIVE EMBODIMENTS

Undesirably, some prior art medical ports distort pressure waveform measurements from in-line transducers. In illustrative embodiments, a gland (also referred to as a resilient valve element) has one or more projections on its surface that are configured to radially support the gland, consequently reducing distortions in blood pressure measurements. Specifically, the inner diameter/surface of a valve housing compresses the projections, radially inwardly compressing the gland. The radially inward compression stiffens the gland, reduces waveform distortion, and ultimately provides better pressure waveforms measurements, for example, from an in-line pressure transducer. Details of illustrative embodiments are discussed below.

Figure 1:
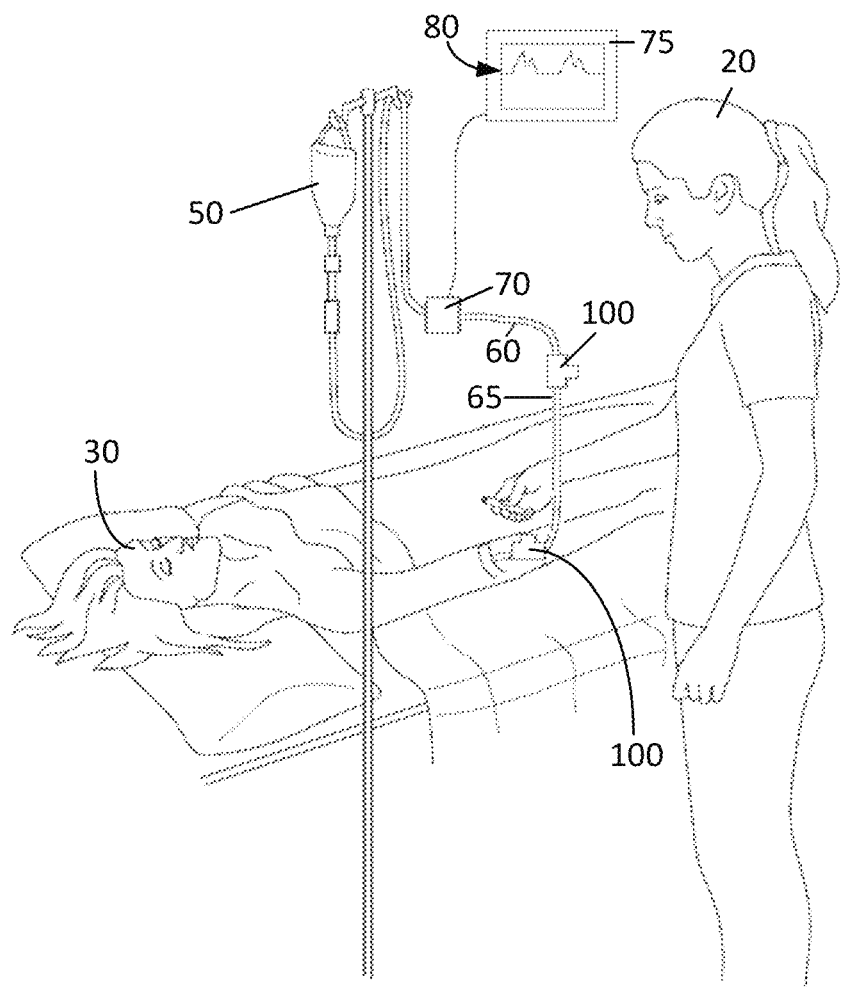
FIG. 1 schematically shows use of a medical valve in-line with a pressure transducer, in accordance with illustrative embodiments of the invention.

FIG. 1 schematically shows use of a medical valve in-line (also referred to as "valve 100") with a pressure transducer in accordance with illustrative embodiments of the invention. As shown, the medical valve 100 may be connected to sections of tubing 60 and 65 extending between a patient 30 and a fluid bag 50 (e.g., on a fluid bag stand). Among other things, that tubing 60 and 65 may couple with the valve 100 by bonding, welding, press-fit, etc.

In some applications (e.g., in critical care applications), the medical practitioner 20 (e.g., a nurse 20) may need to monitor venous or arterial pressure of the patient 30 (e.g., the intra-venous or intra-arterial blood pressure). Therefore, in some instances, the fluid transfer set may also include a pressure transducer 70 (i.e., a sensor) with a strain gauge that measures the pressure waveform within the artery or vein. The pressure is converted to an electrical signal that ultimately is forwarded to a monitor 75. The monitor 75, in turn, may display a graphic 80 representing the intra-arterial or intra-venous blood pressure waveform of the patient 30. A healthcare provider, such as the nurse 20, then may check the patient's 30 blood pressure waveform as a means to assess the status of the patient 30.

Figure 2:
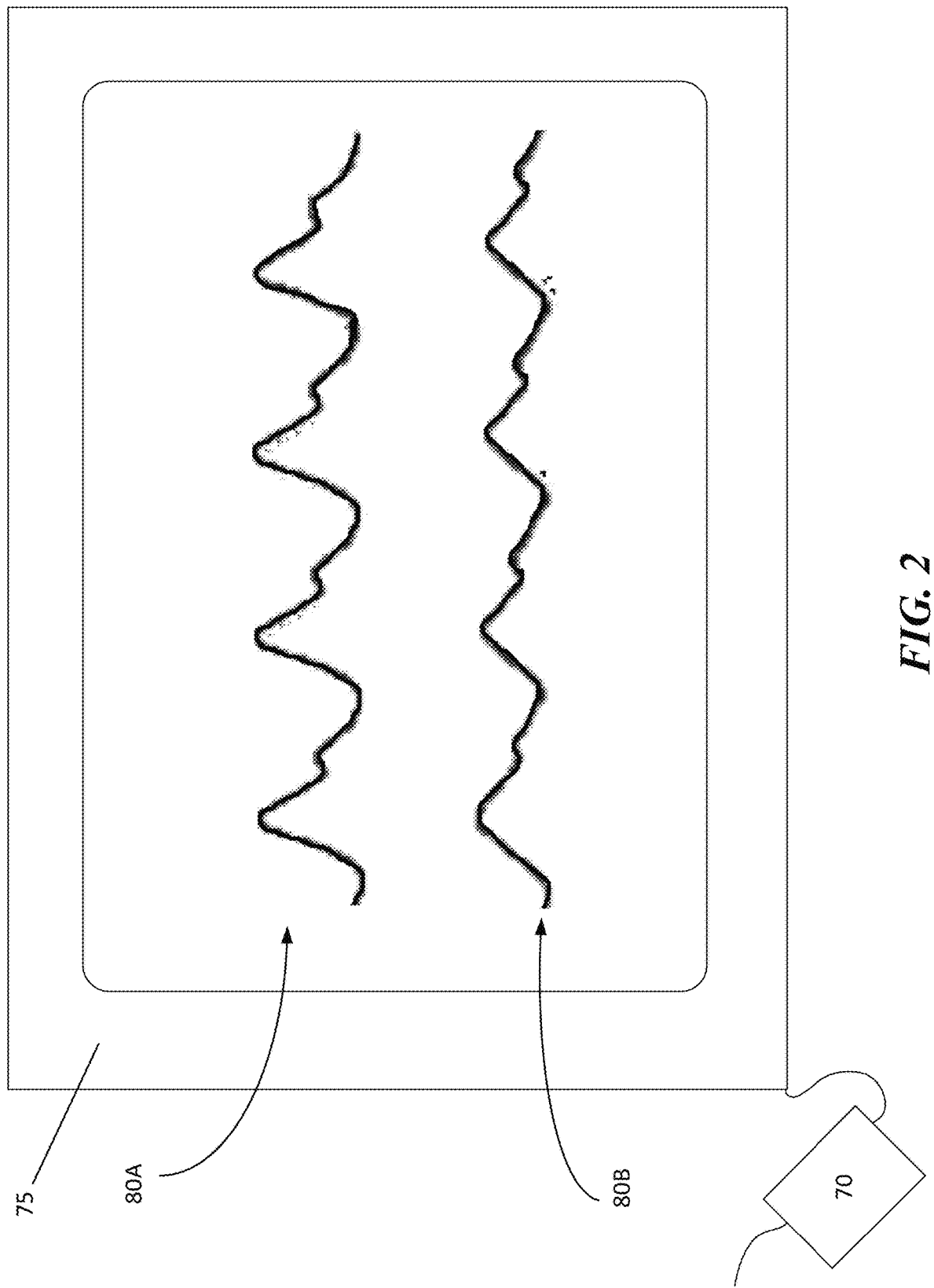
FIG. 2 schematically shows a normal blood pressure reading and a distorted blood pressure reading.

FIG. 2 schematically shows examples of a normal blood pressure waveform reading 80A and a distorted blood pressure waveform reading 80B. Although shown simultaneously in the figure, the monitor 75 generally displays only a single graphic 80 (also referred to as waveform 80). The two different graphics 80A and 80B are shown on the same monitor 75 for purposes of this description. Thus, waveform 80 appears either as normal waveform 80A or as distorted waveform 80B, but not both simultaneously. The graphic 80 therefore effectively may be considered to be output by the transducer 70, as described above.

The inventors discovered that normal blood pressure readings 80A undesirably may become the distorted blood pressure readings 80B when transducers 70 are in-line and in fluid communication with some medical ports. To mitigate that problem, illustrative embodiments have a gland 105 with at least one projection 110 configured to maintain compressive contact with an inner surface of a valve housing 106 to significantly mitigate waveform 80 distortion (e.g., the appearance of the waveform 80 as the distorted waveform 80B).

Figure 3A:
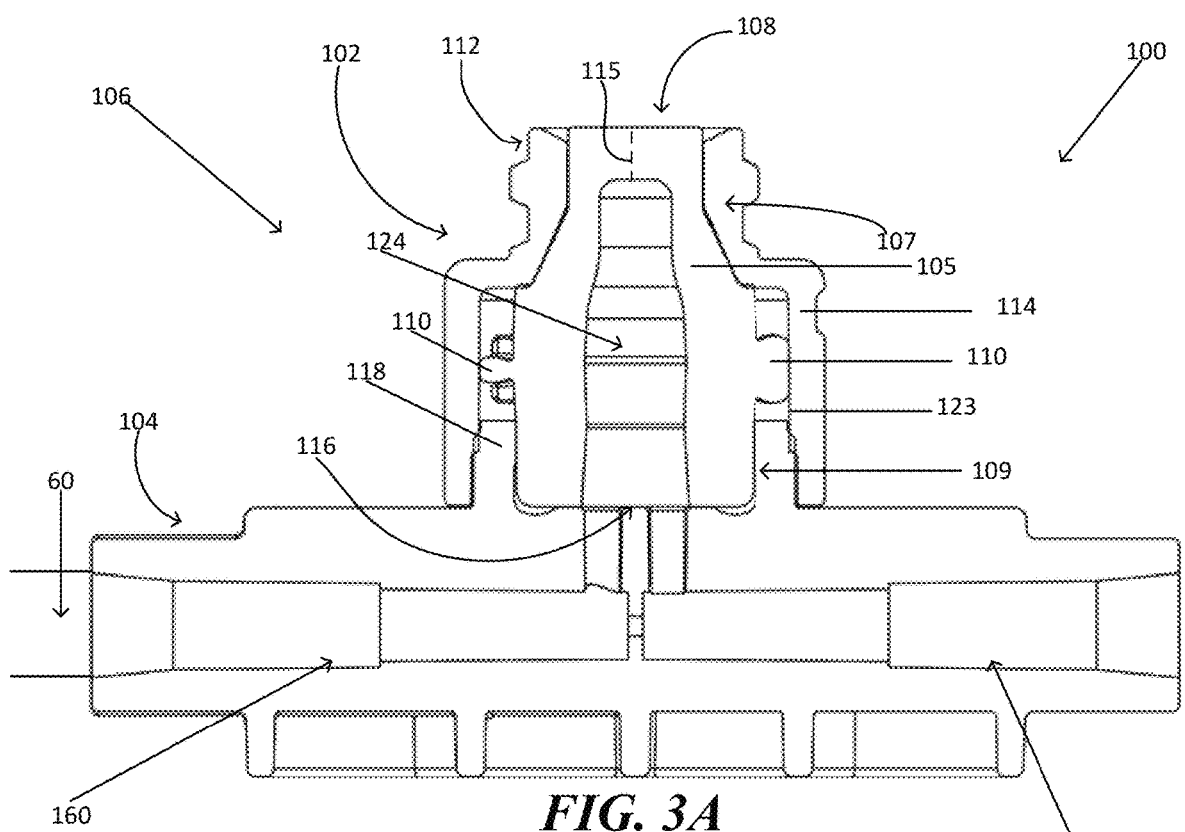
FIG. 3A schematically shows the in-line medical valve of FIG. 1 in a closed mode, in accordance with illustrative embodiments of the invention.

FIG. 3A schematically shows a cross-sectional view of an illustrative embodiment of the valve 100 of FIG. 1 in a closed mode. The valve 100 has the noted housing 106 formed by an inlet housing 102 coupled with an outlet housing 104. These two housings 102 and 104 may be coupled by any of a variety of techniques, such as via ultrasonic welding and/or a snap-fit connection. The housing 106 forms an interior chamber that contains the above noted gland 105, which normally closes (e.g., seals) an opening 108 of the inlet housing 102. The valve 100 is considered to be in the closed mode when the opening 108 is sealed. It should be further understood that although illustrative embodiments describe a closed mode that prevents fluid flow, the closed mode may only significantly mitigate fluid flow.

In accordance with preferred embodiments, the gland 105 (also referred to as a resilient valve element 105) has a body that forms a lumen 124, and a radially outwardly extending projection 110 that mitigates the prior noted signal distortion. Specifically, as described previously, the in-line transducer 70 may take a pressure measurement via a first fluid channel 160 connected to the tubing 60. When pressure measurements are taken, the valve 100 is generally in the closed mode shown in FIG. 3. As discussed in greater detail below, the projection 110 cooperates with the interior chamber to produce a more accurate waveform, such as waveform 80A of FIG. 2.

The housing 106 also includes a proximal portion 112 and a valve wall 114 that extends distally from the proximal portion 112. As shown in FIG. 3, the valve wall 114 has an interior contact surface 123 that cooperates with the projection 110. The gland 105 also has a distal portion 109 that preferably is open to form a distal port 116 in, or proximate to, the inlet housing 102. To help support the gland 105, the outlet housing 104 has an annular wall 118 that contacts the distal portion 109 of the gland 105. As discussed in greater detail below, fluid (e.g., medication, saline, blood, etc.) flows through the lumen 124 of the valve 100 via the distal port 116 of the gland 105.

Figure 5:
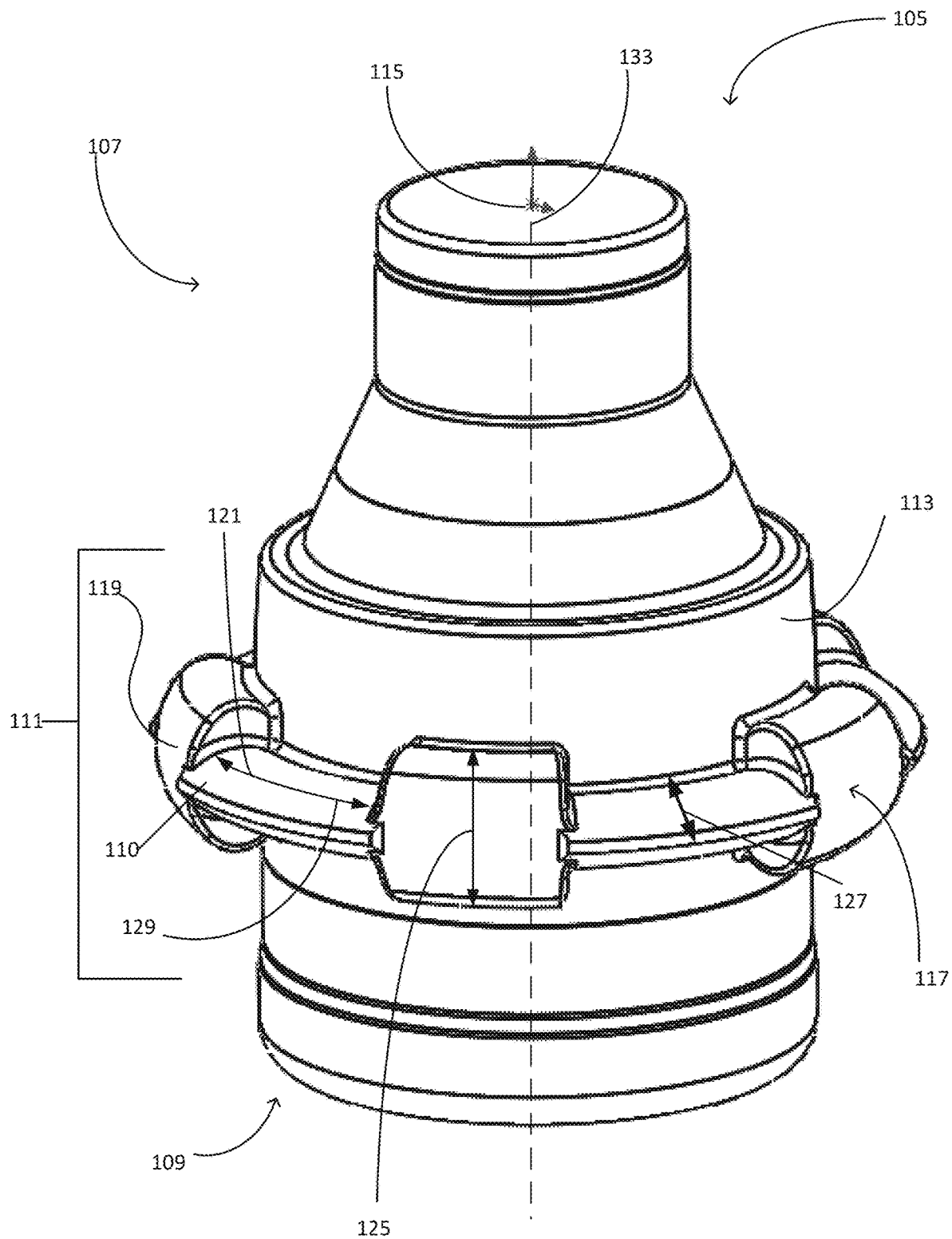
FIG. 5 schematically shows a perspective view of the gland of FIGS. 3-4 in an unconstrained state, in accordance with illustrative embodiments of the invention.

The gland 105 thus may be considered to have a body with a proximal portion 107, the noted distal portion 109, and a central portion 111 (as shown in FIG. 5) between the proximal and distal portions 107 and 109. In some embodiments, the proximal portion 107 of the gland 105 is generally flush with the proximal portion 112 of the housing 106. The proximal portion 107 of the gland 105 and the proximal portion 112 of the housing 106 thus present a swabbable surface, i.e., it may be easily wiped clean with an alcohol swab, for example, or other swab.

The opening 108 preferably is compatible with a luer taper and is configured to allow the medical practitioner 20 to draw a sample from the valve interior 122. To that end, the gland 105 includes a resealable aperture 115 extending through at least a part of the proximal portion 107. Among other things, the aperture 115 may be a pierced hole or a slit. Alternatively, the proximal portion 107 may be molded with the aperture 115. When the gland 105 is in the closed mode (i.e., preventing passage of fluid), as shown in FIG. 3, the aperture 115 may be held closed by radially inwardly directed pressure of the inner surface of the opening 108. In that case, the inner diameter of the opening 108 may be smaller than the outer diameter of the proximal portion 107 and thus, squeezes the aperture 115 closed. Alternatively, the gland 105 (e.g., the proximal portion 107) may be formed so that the aperture 115 normally stays closed in the absence of radially inward force provided by the inner diameter of the opening 108. In other words, the proximal portion 112 may be formed so that the aperture 115 normally is closed.

Figure 3B:
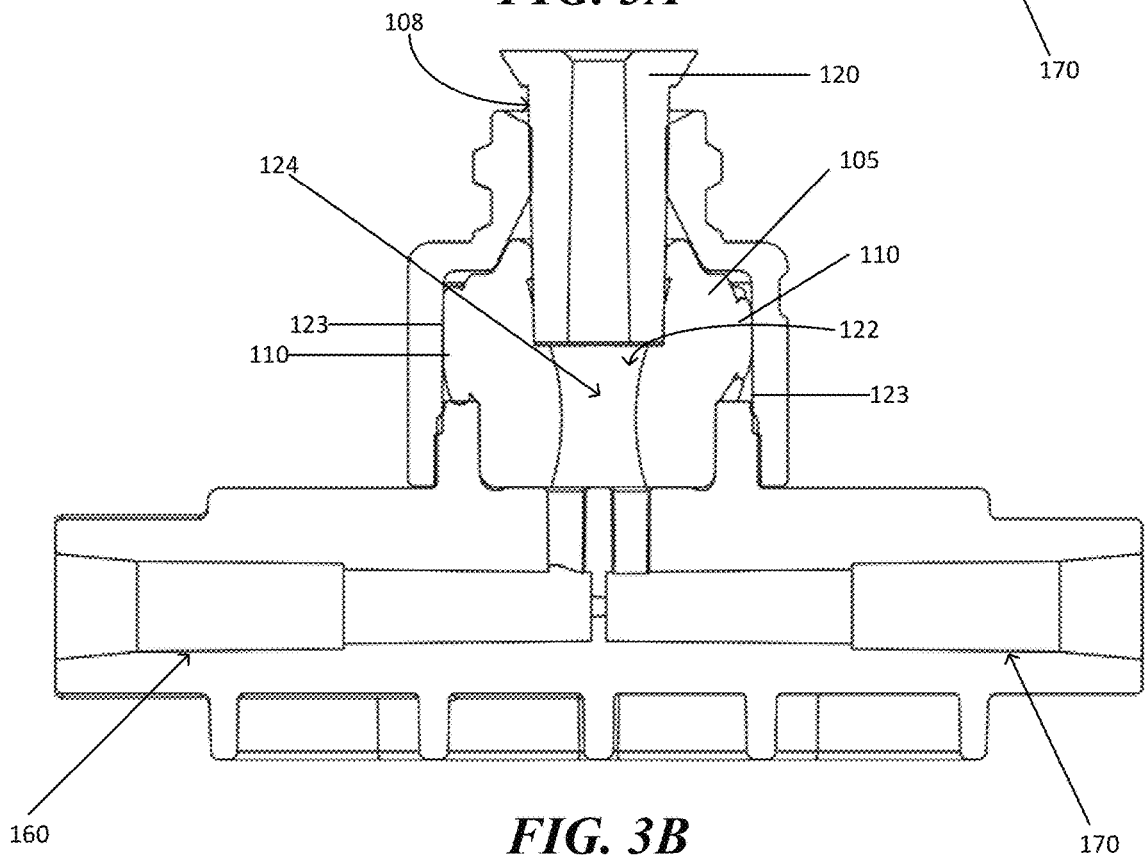
FIG. 3B schematically shows the in-line medical valve of FIG. 3A in an open mode, in accordance with illustrative embodiments of the invention.

FIG. 3B schematically shows a cross-sectional view of the valve 100 of FIG. 3A in the open mode in accordance with illustrative embodiments of the invention. During operation (e.g., when taking a sample from the valve 100), the medical practitioner 20 may insert the medical implement 120 (e.g., a syringe) into the opening 108 of the housing 106. As the medical implement 120 is inserted, the gland 105, which normally closes the opening 108, moves/deforms distally within the housing 106. As the gland 105 continues to move/deform distally into the housing 106, the aperture 115 opens (e.g., when the proximal portion 107 of the gland 105 enters the larger inner diameter portion of the proximal portion 112 of the housing 106) to create fluid communication between the medical implement 120 and the lumen 124. Conversely, when the medical implement 120 is withdrawn from the opening 108 (e.g., after sampling is complete), the elastomeric properties of the gland 105 cause the gland 105 to begin to move proximally within the housing 106 and return to its at-rest position with the proximal portion 107 within (and closing) the opening 108.

The valve 100 has a plurality of fluid channels extending through the housing 106 that allow 1) fluid to flow through the valve 100 and 2) the sample to be taken through the opening 108. For example, the housing 106 may form a second fluid channel 170 that effectively is the mirror image of the first fluid channel 160. The first fluid channel 160 fluidly connects the lumen 124 with the tubing 60, while the second fluid channel 170 fluidly connects the lumen 124 and the other tubing 65 (see FIG. 1). As shown, both fluid channels in this embodiment have a larger horizontal portion and a smaller vertical portion (from the perspective of the figures). In this manner, when primed, fluid flows through the first fluid channel 160, into the lumen 124, and out of the valve 100 through the second fluid channel 170 and tubing 65. Similarly, fluid may flow through the plurality of fluid channels of the sampling port 100 in the opposite direction.

As noted above, absent the projections 110, the inventors discovered that pressure readings from the transducer taken in-line with the valve 100 become distorted (e.g., dampened). The inventors deduce that this distortion principally occurs as a result of movement by the unsupported body of the gland 105 (e.g., the central portion 111) in response to pressure within the lumen 124, due in part to the relatively large surface area within the lumen 124. Illustrative embodiments compensate for the distortion in the waveform 80 measurement by providing the noted projections 110 on the outside surface of the gland 105. In some embodiments, when in the closed mode, these projections 110 abut the inner surface of the inlet housing 102 and increase inward radial compression around a significant circumferential portion of the gland 105 (compared to gland compression when not within the inlet housing 102). The inventors recognized that this gland stiffening/reinforcement across a rather large surface area improves the fidelity of the output waveform 80—preferably causing it to look closer to waveform 80A of FIG. 2.

As contrast, FIG. 5 schematically shows a perspective view of the gland 105 of FIGS. 3-4 in an unconstrained state in accordance with illustrative embodiments of the invention. The gland 105 may be considered to have a central axis 133 running longitudinally through the proximal portion 107, a central portion 111, and the distal portion 109. In the unconstrained state, no portion (107, 109, or 111) of the gland 105 is compressed (e.g., the gland 105 is not in the housing 106).

The central portion 111 of the gland 105 includes a wall 113 having at least one projection 110 thereon. Illustrative embodiments may refer to a plurality of projections 110, but it should be understood that the various embodiments described with reference to a plurality of projections 110 also apply to a singular projection 110, and vice-versa. In some embodiments, each projection 110 may be shaped, for example, as a strip, such as a full ring, and/or a tab/flap of material. The projections 110 may be formed from the same material as the gland 105, a different material, or from a combination of materials. For example, the projections 110 may be overmolded from a stiffer durometer material using a two-shot molding process. Furthermore, the projections 110 may be molded with the gland 105 or attached (e.g., using adhesive). Preferably, the projections 110 are of similar durometer or stiffer durometer than the gland 105 body itself, to help compress the gland 105 body. In illustrative embodiments, at least a portion of the projections 110 are concyclic on the wall 113.

As noted above, the projections 110 are configured to come into, and maintain, compressive contact with the inner contact surface 123 of the housing 106 (e.g., the inner surface of the valve wall 114, see FIGS. 3-4) when the gland 105 is in the housing 106. Some embodiments may tune the projections 110 to provide varying amounts of compressive contact. To that end, illustrative embodiments of the projections 110 may have variable thickness 125 (measured along the central axis 133), height 127 (e.g., distance from the wall 113 measured transverse to the central axis 133), and width/arc 129 configured to provide various amounts of compressive contact with the contact surface 123. The dimensions (e.g., circumference) of the contact surface 123 also factor into the amount of radial compression on the gland 105. In illustrative embodiments, the projections 110 may contact the contact surface 123 in the open mode and in the closed mode. Furthermore, the projections 110 may have compressive contact with the contact surface 123 in the open mode and/or in the closed mode.

The compressive contact on the projections 110 provides the noted stiffening, inward radial compression on the gland 105. Generally, compressing the gland 105 with projections 110 on opposite sides (e.g., 180 degree separation) provides compressive contact. However, it should be understood that a variety of different projection 110 locations and contact surface 123 areas are sufficient to provide compressive contact. Compressive contact (e.g., at the central portion 111) stiffens the gland 105 and reduces distortion in the pressure wave readings. Compressive contact may cause compression of the height 127 of the projection 110 and/or in the outer diameter of the wall 113. Additionally, compressing the height 127 may increase the thickness 125 of the projection 110. For example, interference between the outer diameter 130 of the projection 110 and the inner diameter 132 of the contact surface 123 causes compressive contact (see FIG. 8). The gland 105 is compressed radially inwardly as a result of the interference. A single projection 110 and/or a plurality of projections 110 may have, but do not require, a uniform height 127. Furthermore, illustrative embodiments may have, but do not require, that the projections 110 are offset by 180 degrees.

FIG. 4A schematically shows a gland of the prior art that is uncompressed by the inner diameter of the housing. FIGS. 4B-4H schematically show cross-sectional views of various embodiments of the gland 105 within the housing 106, in accordance with illustrative embodiments of the invention. FIG. 4A schematically shows a prior art gland without any projections. FIGS. 4B-4C schematically show the gland wall 113 having projections 110 that are in translational contact (i.e., the wall 113 is not squeezed by the contact) with the housing 106.

Compressive contact is distinguishable from translational contact. In some embodiments, the projections 110 on the gland wall 113 form a larger outer diameter than the inner diameter of the contact surface 123. To some small degree, all contact can be said to provide some amount of compression. However, translational contact pushes the gland 105 more than it compresses (e.g., squeezes and/or stiffens) the gland 105. Furthermore, translational contact may provide a single point of contact that directs force inwardly, but it does not provide radially inward compression (except, for example, when the gland 105 is pushed sufficiently to cause it to press against an opposing contact surface 123 as shown for example in FIG. 4D). However, while illustrative embodiments of the gland wall 113 may be compressed between the projection 110 and the contact surface 123 (as shown in FIG. 4D), practically it may be difficult or impossible to insert a luer effectively (e.g., transition from the closed mode to the open mode in a hospital setting is difficult because opening of gland 105 may be offset from the longitudinal axis 133 and the gland body may be warped). In such an instance, the gland 105 cannot be said to be configured to readily open when actuated by a medical implement 120.

FIGS. 4E-4H schematically shows embodiments where the projections 110 provide radially inward compression on the gland wall 113. As shown in FIG. 4E, illustrative embodiments have three or more projections 110 on the surface of the wall 113, that are spread equidistantly around the surface of the wall 113. For example, the center of projections 110 may be separated about approximately 120 degrees on the surface of the gland wall 113. As shown in FIG. 4F, illustrative embodiments may have projections 110 whose centers are separated by approximately 180 degrees on the surface of the gland wall 113.

Furthermore, in some embodiments, the projections 110 may contact between about 90 degrees and about 135 degrees of the circumference of the gland wall 113. Alternatively, as shown in FIG. 4G, in some embodiments the projections 110 may contact between about 225 degrees and about 270 degrees of the circumference of the gland wall 110. Some embodiments may cover more than 270 degrees of the circumference gland wall 113 (e.g., 360 degrees as shown by the full ring projection 110 in FIG. 4H). It should be understood that generally, the more total contact surface area 103 (e.g., as a result of thickness 125 and arc length 129) the less radial interference (e.g., as a result of height 127) required to stiff the gland wall 113 and reduce waveform distortion. In some embodiments, compressing the thickness of the gland wall 113 by at least 1% is sufficient to reduce waveform 80 distortion (e.g., if the gland wall 113 is 0.1 cm thick, compressing the thickness by at least 0.001 cm). Additionally, some embodiments may compress the thickness of the gland wall 113 by at least 2%, 3%, or more. Alternatively, some embodiments may compress the gland wall 113 by less than 1% (e.g., between 1% and 0.001%).

Projections 110, and/or portions (e.g., portions 119 and 121) thereof, may be configured to have variable heights 127, thicknesses 125, and arc lengths/widths 129. As is known in the art, the arc length 129 is calculated by the radius of the arc (e.g., the distance from the central axis 133) multiplied by the angle θ. Adjusting these parameters provides different amounts of inwardly radial compression on the gland 105 when the contact surface 123 compresses the projection 110. In addition, varying these parameters alters the force required by the medical practitioner 20 to insert the medical implement 120 into the opening 108 of the housing 106 and to move/deform the gland 10 (as will be described in further detail below). Preferably, a portion of the projection 110 freely deforms within the interior chamber of the housing 106 as the valve transitions from the closed mode to the open mode.

Furthermore, illustrative embodiments show the gland projections 110 contacting the inlet contact surface 123 in the closed mode and in the open mode. Preferably, the projection 110 contacts the same surface 123 when in the closed mode and in the open mode. For example, the projection 110 may "slide" along the surface 123 to reduce the amount of resistive force required to move the gland from the closed mode to the open mode. In some embodiments, however, the gland projections 110 may contact the contact surface 123 (e.g., inlet contact surface 123) only in the closed mode.

FIG. 5 shows a single projection 110 formed as a non-uniform ring 117. The non-uniform ring 117 has thicker portions 119 (e.g., compression tabs 119) interspersed with thinner portions 121 (e.g., compression strips 121). The portions 119 and 121 have different heights 127, thicknesses 125, and arc lengths/widths 129. However, both of the portions 119 and 121 are part of a single, integrated projection 110. Although FIG. 5 shows a single projection 110 on the central portion 111, it should be understood that illustrative embodiments may have more than one projection 110 on the central portion 111. Additionally, or alternatively, illustrative embodiments may have at least one projection 110 on one or more of the proximal portion 107, the distal portion 109, and the central portion 111.

Figure 6:
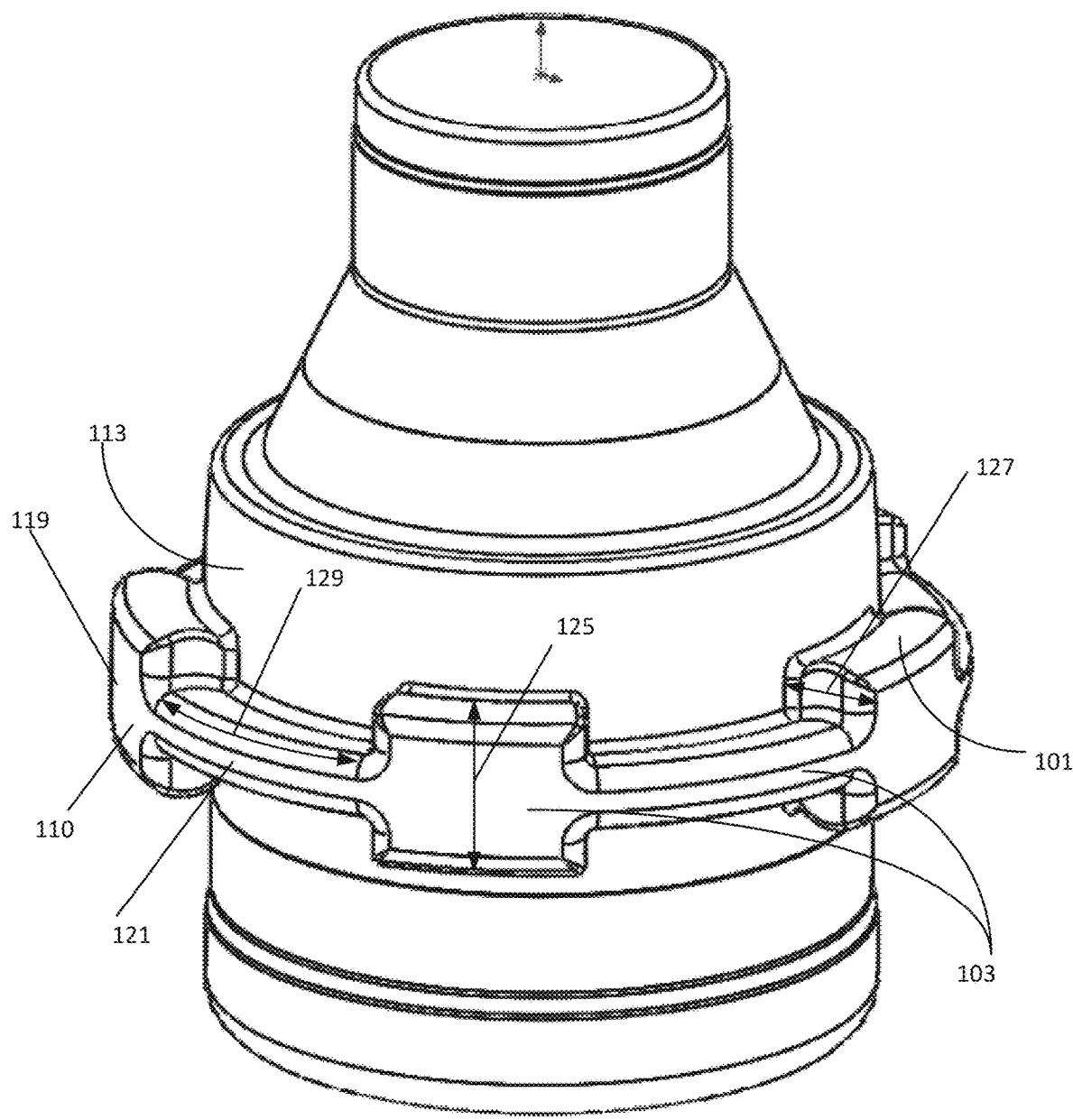
FIG. 6 schematically shows a perspective view of the gland of FIG. 5 in a constrained state (e.g., in the closed mode), in accordance with illustrative embodiments of the invention.

FIG. 6 schematically shows a perspective view of the gland 105 of FIG. 5 in a constrained/compressed state (e.g., in the closed mode), in accordance with illustrative embodiments of the invention. In the constrained state, the gland 105 is within the housing 106 (not shown for visibility of the gland 105) and the contact surface compresses the projections 110. As shown in the figure, both the thicker portions 119 and the thinner portions 121 are compressed (e.g., their height 127 has decreased and their shape has changed). In some embodiments, the thickness 125 and/or width 129 may deform to compensate for the compression over the height 127. Although both portions 119 and 121 of the projection 110 are compressed, illustrative embodiments do not require that the entirety of the projection 110 be compressed. Compressive contact with a portion (e.g., 119 or 121) of one or more projections 110 may cause sufficient inward radial compression. For example, 180 degree opposite sides of the gland 105 may have projections 110 that are compressed.

In some embodiments, the projection 110 (e.g., portions 119 and 121) may be configured to have a total projection contact surface area 103. The projection contact surface area 103 is the portion of the projection 110 that is physically in contact with the contact surface 123 of the housing 106 in the closed mode. For comparison, FIG. 6 shows a projection non-contact surface area 101. As shown, the non-contact surface area 101 is not directly in contact with the contact surface 123 of the housing 106 and may freely deform within the interior chamber of the housing 106 as the valve 100 transitions from the closed mode to the open mode.

Illustrative embodiments may have projections 110 shaped as a non-uniform ring 117 to reduce, relative to a uniform ring 117, the resistive forces on the medical implement 120 when it is inserted into the valve 100 (e.g., when the valve transitions from the closed mode shown in FIG. 3A to the open mode shown in FIG. 3B). The non-uniform ring 117 eases movement of the projection 110 relative to the main body of the gland 105. The ring 117 also provides a reduction in contact area with the contact surface 123 that allows the projection 110 to more easily deform against the contact surface 123 when the medical implement 120 is inserted. Thus, the force that may otherwise be required to insert the medical implement 120 into the valve 100 is reduced.

Figure 7:
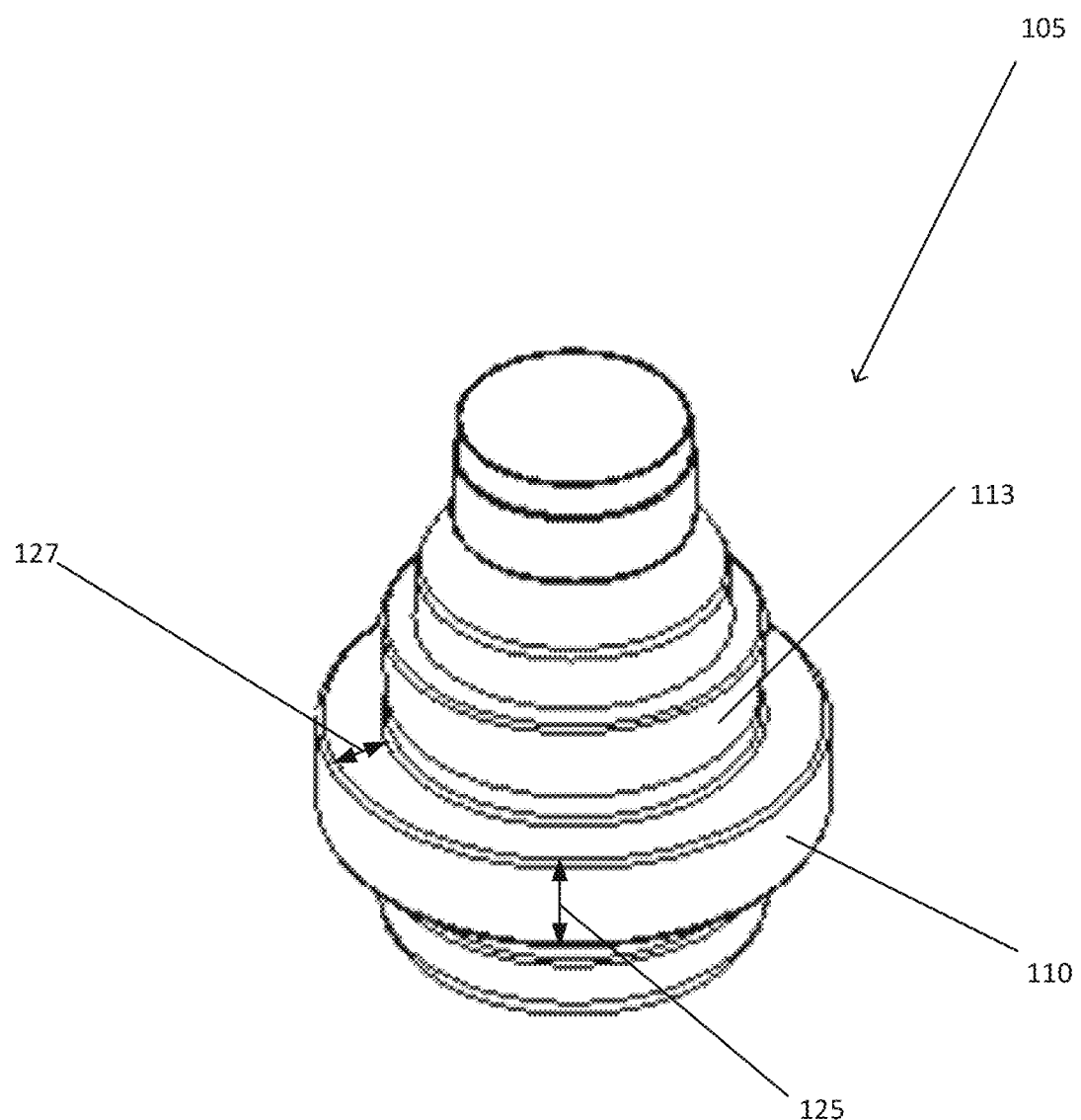
FIG. 7 schematically shows an alternative embodiment of the gland, in accordance with illustrative embodiments of the invention.

FIG. 7 schematically shows an alternative embodiment of the gland 105 in accordance with illustrative embodiments of the invention. The gland 105 may have one more uniform ring projections 110. The projection 110, similar to the projection 110 in FIGS. 5-6, has a thickness 125 and a height 127. However, the projection 110 has a 360 degree arc length 129. When the gland 105 is placed within the housing 106, the projection 110 is compressed along 360 degrees of angular contact. It should be understood that just because the projection 110 is compressed along 360 degrees of angular contact, does not necessarily mean that the gland 105 experiences more inward radial compression than illustrative embodiments that are not compressed a full 360 degrees. The magnitude of compression is based on the dimensions of the projection 110 (e.g., surface area, height 127, thickness 125, arc length 129), the dimensions of the housing 106 (e.g., contact surface 123), and the interference between the projection 110 and the housing 106 (including the amount of angular contact). Those skilled in the art may select those parameters to achieve a desired compression for a given application.

Illustrative embodiments having the 360 degree uniform ring projection 110 undesirably may provide more resistance when inserting the medical implement 120 than is desirable. To mitigate this problem, illustrative embodiments have a non-uninform projection 110 (shown in FIGS. 5-6), or break the single projection 110 into a plurality of projections 110 (e.g., an interrupted ring projection 110—shown in FIG. 9).

Figure 8:
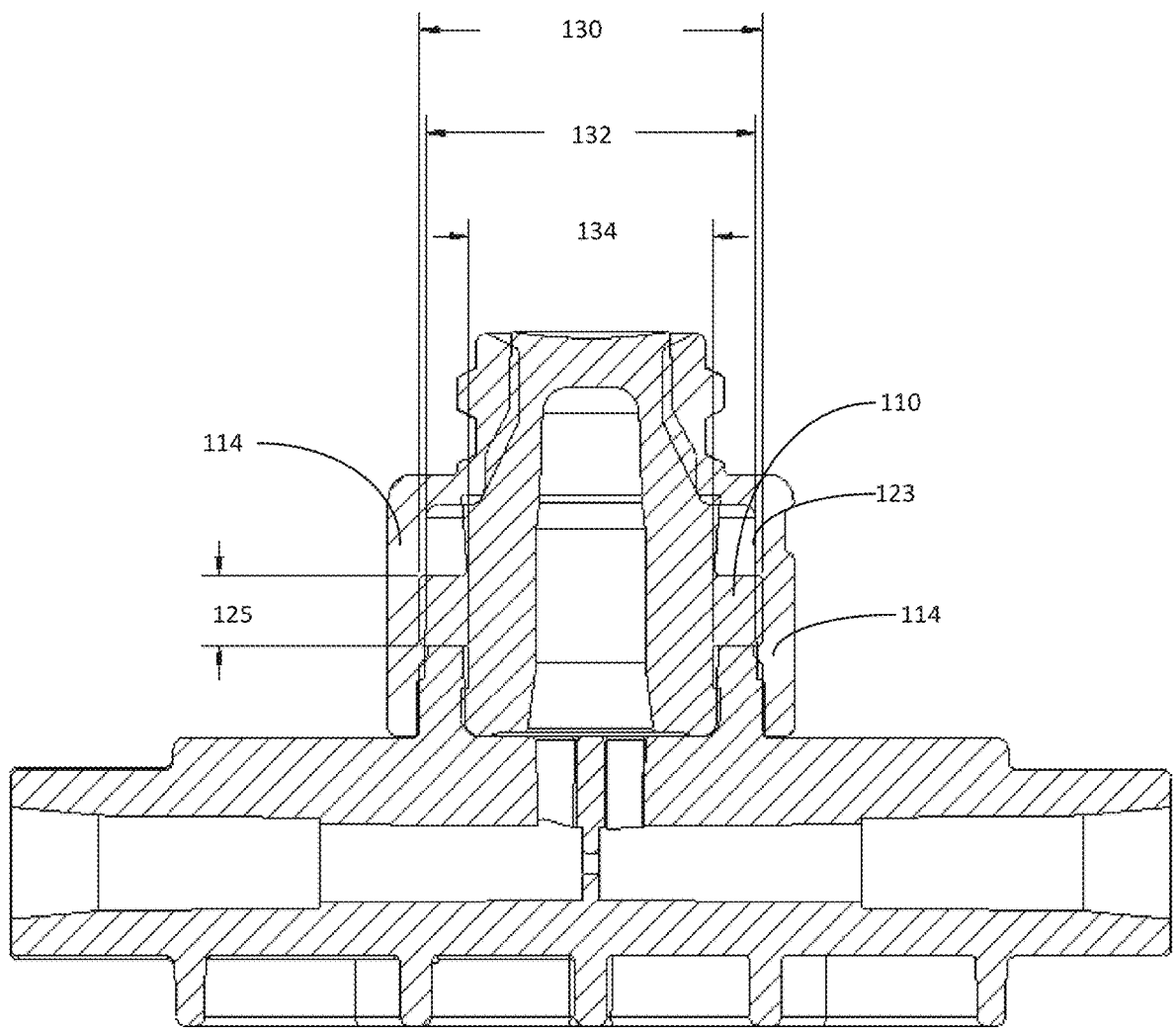
FIG. 8 schematically shows a cross-sectional view of the gland of FIG. 7 constrained within a valve.

FIG. 8 schematically shows a cross-sectional view of the gland 105 of FIG. 7 constrained within its valve 100. As with other embodiments, the contact surface 123 compresses the gland 105 radially inwardly by compressively contacting the projection 110 via interference between the outer diameter 130 of the projection 110 and the inner diameter 132 of the contact surface 123. For example, gland body outer diameter 134 when uncompressed may be 0.279 inches, the ring projection 110 may have an uncompressed outer diameter 130 of 0.392 inches, and the inner diameter 132 of the inlet contact surface 123 may be 0.378 inches. In some embodiments, the projection 110 may be, but is not required to be, formed from a harder durometer material than the gland 105 body, and thus, the gland 105 body may experience radially inward compression. For example, the outer diameter 130 may be compressed about 0.014 inches. Alternatively, the projection 110 may be formed from a similar or lower durometer material as the gland 105, and may, for example, experience a similar compression of about 0.014 inches. For example, it may be easier to insert a medical implement 120 into the gland 105 (e.g., to facilitate translation from the closed mode to the open mode) if the projection 110 is made of a lower durometer material. The above described dimensions are merely exemplary and not intended to limit illustrative embodiments of the invention. Furthermore, based on the materials of the gland 105, the projection 110, and the housing 106, all of the components may experience a change in their dimensions (e.g., the projection 110 may compress, the gland 105 body may compress, and/or the inlet housing 102 may expand albeit minutely on a relative basis).

In some embodiments, the gland body outer diameter 134 may be compressed between about 0.01 inches and about 0.03 inches. More specifically, the gland body outer diameter 134 may be compressed about 0.015 inches and about 0.025 inches. In some embodiments, the amount of diametric interference between the projection 110 (e.g., ring projection 110) and inlet inner diameter 132 is less than 0.002 inches per side (0.004 inches per diameter). It should be understood that the more contact surface area 103 the projection 110 has (e.g., thickness 125) the less diametric interference required to effectively stiffen the gland 105. A larger contact surface area 103 for the projection 110 is preferred, as the larger contact surface area 103 requires less diametric inward compression to stiffen the gland 105. That large contact surface area 103 should be balanced against frictional resistance between the gland and the inlet housing 102 when inserting and removing the medical implement 120, as well as the ability of the projection 110 to freely deform within the interior chamber of the housing 106.

In FIG. 8, the outer diameter 130 of the projection 110 is shown as overlapping the inner diameter 132 of the inlet housing 102 and the contact surface 123. However, this is merely to illustrate interference between the outer diameter 130 and the inner diameter 132. It should be understood that in actuality, the gland 105 is compressed by the valve wall 114 and the outer diameter of the projection 110 does not extend into the valve wall 114.

Figure 9:
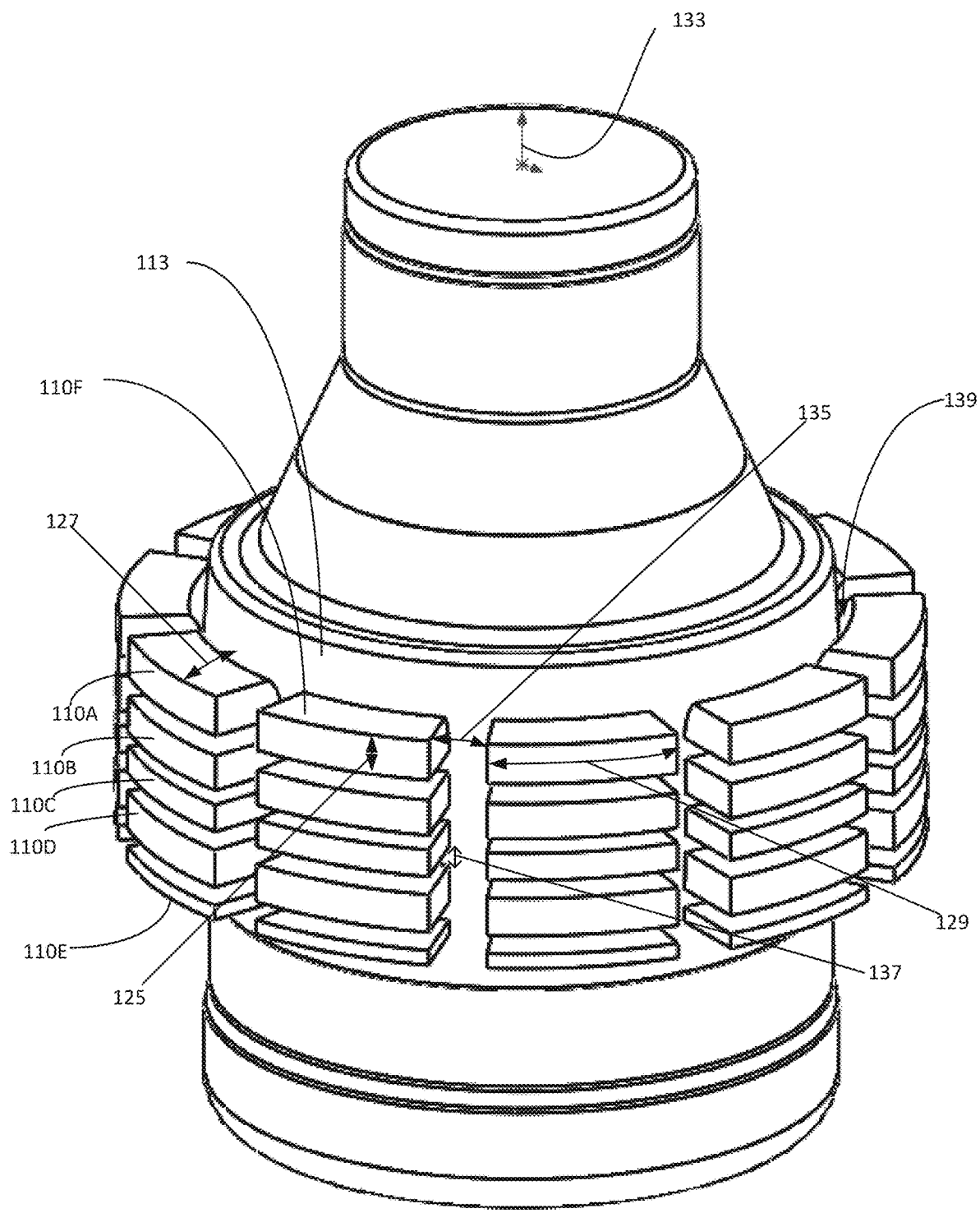
FIG. 9 schematically shows yet another alternative embodiment of the gland having interrupted ring projections, in accordance with illustrative embodiments of the invention.

FIG. 9 schematically shows yet another alternative embodiment of the gland 105 in accordance with illustrative embodiments. As shown in the figure, the projections 110 form a plurality of interrupted rings. For example, projections 110A, 110F, and the other projections 110 coplanar along the central axis 133 form a first ring. Projection 110A and 110F are spaced radially with respect to the central axis 133. Projection 110B and the other projections 110 spaced radially along the central axis 133 form a second ring.

Illustrative embodiments may contain a plurality of different projections 110A-110E that are shaped differently. Although all of the projections 110A-110E have the same height 127 and widths 129, they have varying thicknesses 125. Illustrative embodiments may have projections 110 of varying heights 127, widths 129 and/or thicknesses 125. Furthermore, illustrative embodiments may be spaced along the central axis 133 with varying intervals. For example, projection 110E is spaced further away from projection 110D with respect to the central axis 133 than projection 110B is spaced from projection 110C. A radial interstice 135 (e.g., a space) is formed between radially spaced apart projections (e.g., 110A and 110F). A longitudinal interstice 137 is formed between projections 110 spaced apart along the central axis 133 (e.g., 110A and 110B).

As described earlier, rather than a single thick ring for the projection 110, some embodiments use a plurality of projections 110 to reduce frictional resistance to longitudinal gland 105 movement, enabling the gland 105 more free longitudinal movement in use. Furthermore, projections having a thickness 125 that is smaller than the height 127 are more prone to bending during longitudinal movement of the gland 105, thus, offering the potential for less resistance when inserting the medical implement 120. To that end, in some embodiments, the height 127 may be larger than the thickness 125. Alternatively, in some embodiments, the thickness 125 may be larger than the width 127. Furthermore, in some embodiments, the projections 110 may have reduced attachment surface area with the gland wall 113. For example, projection 110A has a beveled 139 attachment surface. Additionally, or alternatively, some projections 110E may be formed from thin pieces of material. Although the figure shows the interstices 135 and 137 aligned in columns and rows, it should be understood that the interstices 135 and 137 and are not required to be aligned. For example, projections 110 may overlap with interstices along the central axis 133 or radially. Furthermore, projections 110 are not required to be aligned in columns and/or rows.

Figure 10:
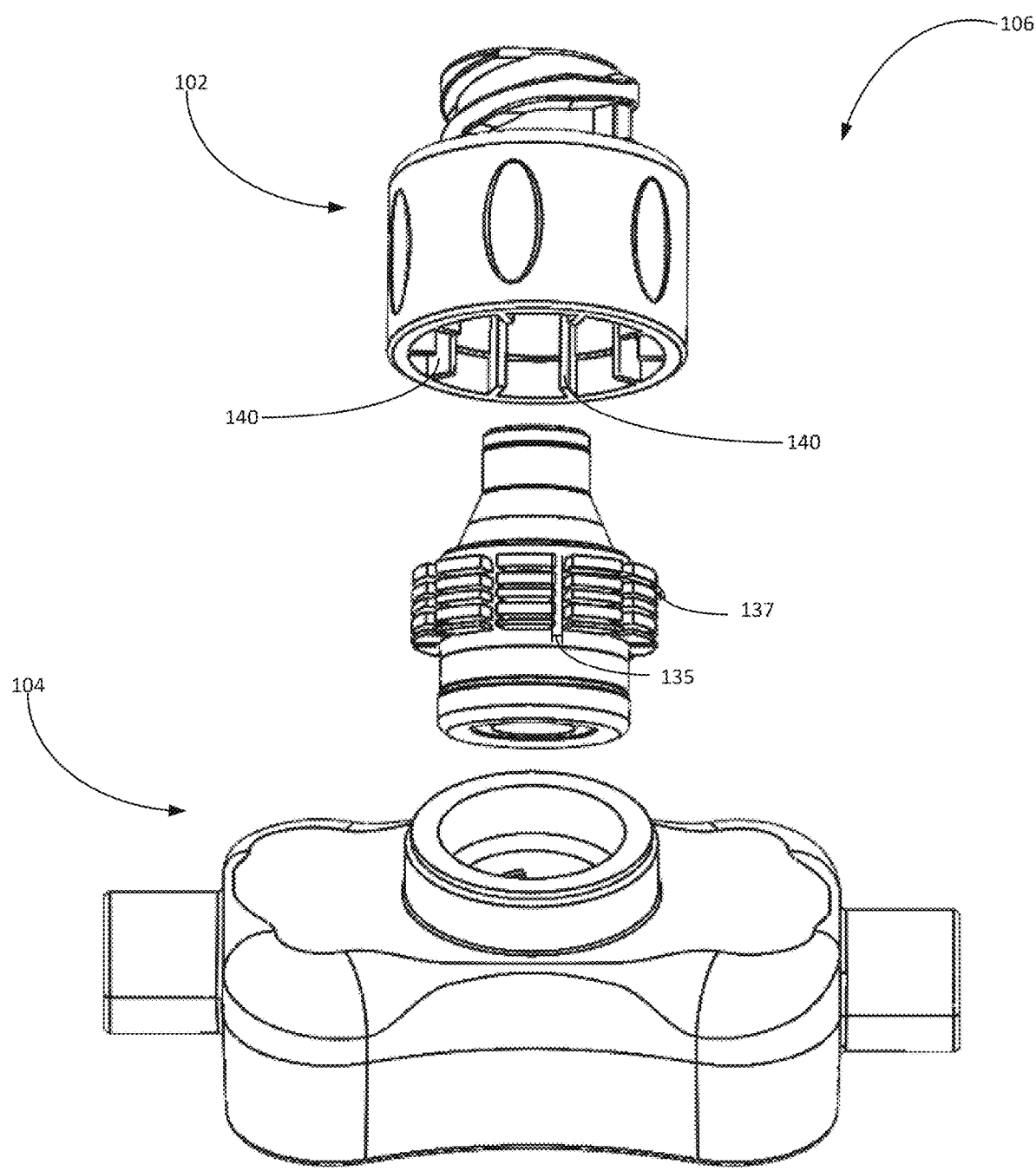
FIG. 10 schematically shows the gland of FIG. 9 used with an alternative embodiment of the housing.

FIG. 10 schematically shows the gland 105 of FIG. 9 used with an alternative embodiment of the housing 106 in accordance with illustrative embodiments of the invention. The inlet housing 102 and/or the outlet housing 104 may have housing projections 140 on their inner surfaces that are directed radially inwardly. In some embodiments, the housing projections 140 may be formed as ribs. Furthermore, the housing projections 140 may be configured to align with the radial interstices 135 and/or longitudinal interstices 137. It should be understood that radial interstices 135 are called "radial" because they are formed between radially spaced projections 110. In a similar manner, longitudinal interstices 137 are "longitudinal" because they are formed between longitudinally spaced projections 110. Alternatively, some embodiments may have housing projections 140 without any gland projections 110. It should be understood that although illustrative embodiments are shown as having housing projections 140 on the inlet housing 102, the housing projections 140 additionally, or alternatively, may be on the outlet housing 104.

Figure 11:
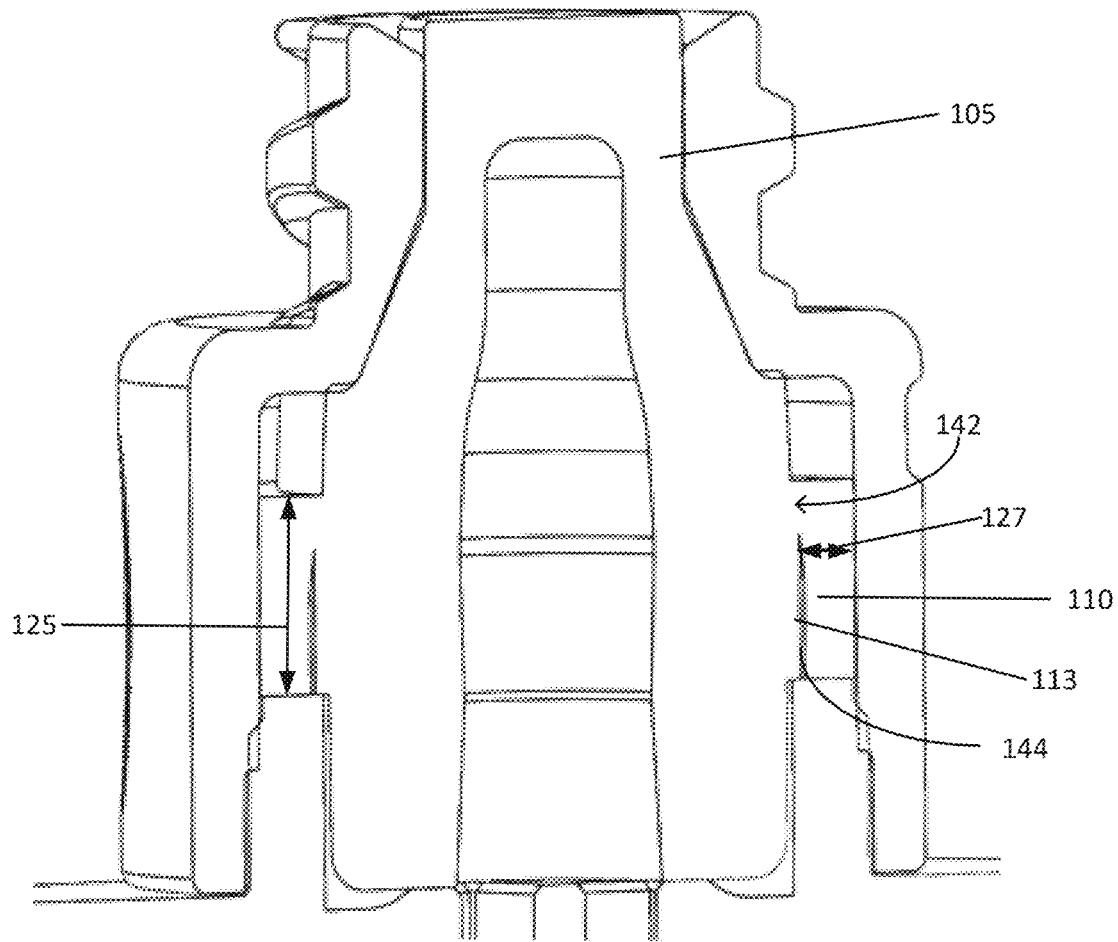
FIG. 11 schematically shows an alternative embodiment of the gland with projections having a slip plane, in accordance with illustrative embodiments of the invention.

FIG. 11 schematically shows an alternative embodiment of the gland 105 in accordance with illustrative embodiments of the invention. The projection 110 may have a small point of attachment 142 relative to its thickness 125. The remainder of the space between the projection 110 and the gland wall 113 may form a slip plane 144 that allows the projection 110 to move freely relative to the body of the gland 105 when a medical implement 120 is inserted. The slip plane 144 reduces the amount of force required to insert the medical implement 120 into the valve 100. Illustrative embodiments may have multiple projections 110 offset radially and/or longitudinally, and one or more of the projections 110 may have slip planes 144.

Figure 12:
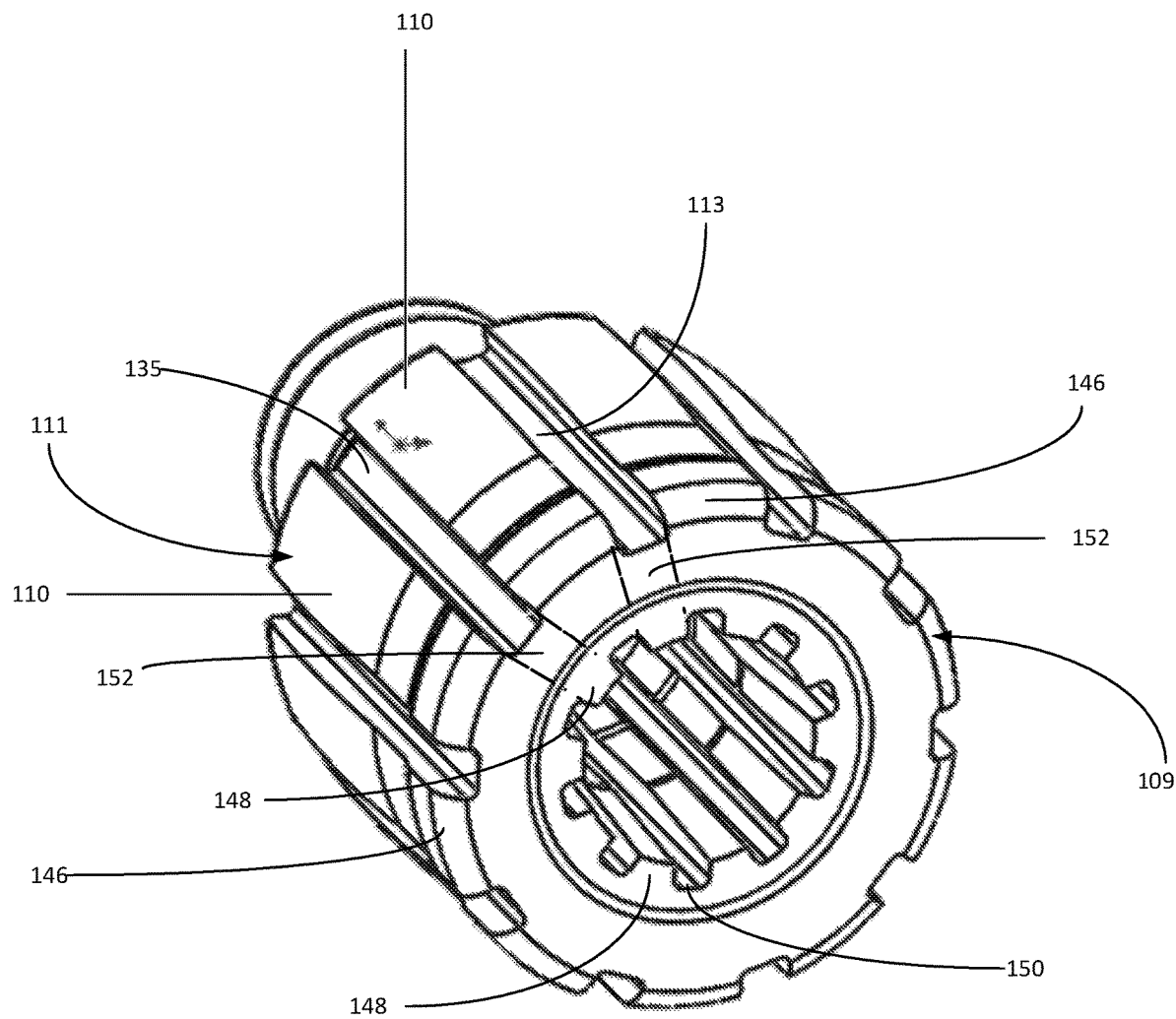
FIG. 12 schematically shows a distal perspective view of an alternative embodiment of the gland having internal ribs, in accordance with illustrative embodiments of the invention.

FIG. 12 schematically shows a distal perspective view of an alternative embodiment of the gland 105 having internal ribs 148, in accordance with illustrative embodiments of the invention. The internal ribs 148 help maintain the integrity of the gland 105 by adding thickness to the gland wall 133. As with other embodiments, the plurality of radial interstices 135 are formed between radially spaced projections 110. As shown, the projections 110 may extend substantially along the entire length of the central portion 111. Furthermore, the gland 105 may have distal projections 146 on the distal portion 109.

To reinforce the thickness of the wall 113, internal ribs 148 may be formed on the inner surface 150 of the gland wall 113. The internal ribs 148 may assist with uniformity of deformation when the medical implement 120 is inserted. In illustrative embodiments, the ribs 148 may be aligned 152 with the interstices 135 and/or 137. The ribs 148 as shown align with the radial interstices 135. Additionally, or alternatively, the ribs 148 may align with the longitudinal interstices 137 (not shown).

In some embodiments, one or more projections 110 may be on any of the proximal portion 107, the central portion 111, and/or the distal portion 109. Furthermore, to aid with stiffening the gland, the proximal portion 107 and/or the distal portion 109 may be constrained by the housing 106.

In some embodiments, the projection 110 may be part of the gland 105 (e.g., molded with or attached via adhesive), a separate piece, or may be part of the inner diameter 132 of the valve 100.

Figure 13:
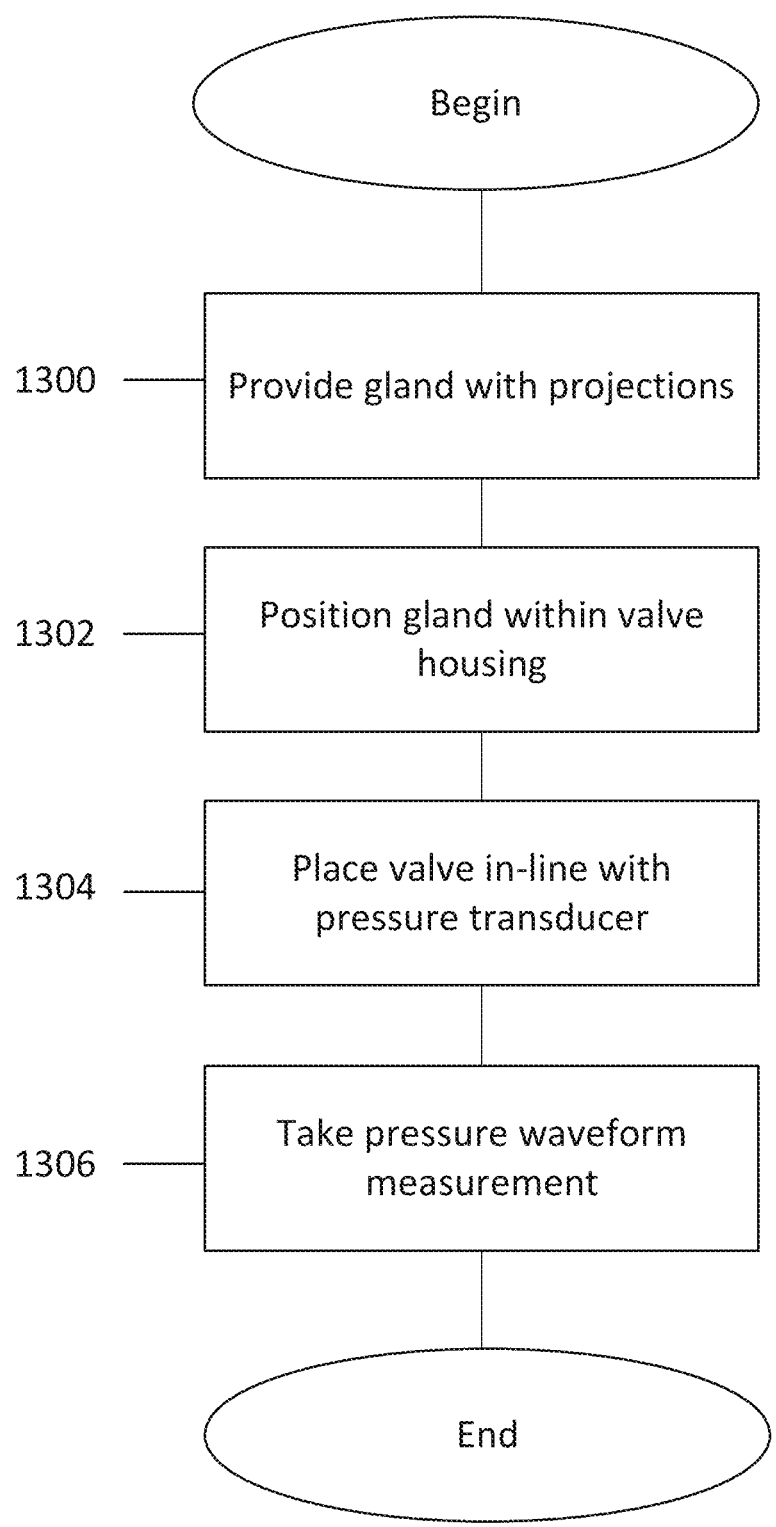
FIG. 13 shows a process of measuring the pressure waveform, in accordance with illustrative embodiments of the invention.

FIG. 13 shows a process of measuring the blood pressure waveform 80, in accordance with illustrative embodiments of the invention. It should be noted that this process may be, in some instances, substantially simplified from a longer process of measuring a pressure waveform 80. Accordingly, the process of measuring a waveform 80 typically has other steps that those skilled in the art likely also would use. In addition, some of the steps may be performed in a different order than that shown, or at the same time. Those skilled in the art therefore can modify the process as appropriate.

The process of FIG. 13 begins at step 1300, in which the gland 105 having projections 110 is provided. As described previously, the projections 110 may take many forms, such as a complete ring, a non-uniform ring, an interrupted ring, and/or combinations thereof. Furthermore, the projections 110 may cover at least along 45 degrees of the circumference of the gland 105. It should be understood that the term "cover," as used in this application, does not necessarily mean the projection 110 spans the entire length of the central portion 111. Instead, the term "cover" is used to refer to the angle of radial coverage (out of 360 degrees) around the gland wall 113. Thus, two opposing projections 110 with an arc length of 30 degrees, even if they are offset along longitudinally (e.g., in a direction along the central axis 133 of the gland 105) may be said to cover 60 degrees of the wall 113. However, in some embodiments, all of the coverage values described in this application may be concyclic, i.e., the projections 110 are formed on a common circle around the gland wall 113. Illustrative embodiments above describe details of the projections 110.

The process then positions the gland 105 within the valve housing 106 at step 1302. In some embodiments, a medical practitioner 20 may position the gland 105 within the valve housing 106. In preferred embodiments, the manufacturer positions the gland 105 within the housing 106, and sterilizes the valve 100 at that time, prior to packaging and shipping. When the valve 100 is positioned inside the housing 106, the projections 110 are compressed radially inwardly by the contact surface 123 of the housing 106. This compressive contact stiffens the gland 105.

Next, at step 1304, the valve 100 is used with the patient 30, preferably in line with a pressure transducer 70. The medical practitioner 20 may set up the valve 100 and/or the pressure transducer 70. When the valve 100 is in the closed mode, a pressure waveform reading 80 may be taken, as described with reference to FIG. 2.

Next, at step 1306, a pressure waveform measurement 80 may be taken. Because the gland 105 was stiffened in step 1302, artifacts that may otherwise appear in the pressure waveform measurement 80A are reduced. Accordingly, the medical practitioner 20 has access to more accurate pressure waveform measurements 80A and may provide better medical care.

Although the above discussion discloses various exemplary embodiments of the invention, it should be apparent that those skilled in the art can make various modifications that will achieve some of the advantages of the invention without departing from the true scope of the invention.

What is claimed is:

1. A medical valve having an open mode that permits fluid flow, and a closed mode that prevents fluid flow, the medical valve configured to be used in-line and in fluid communication with a pressure transducer, the medical valve comprising:
    a housing having an inlet and an outlet, the housing having an interior contact surface at and/or between the inlet and/or the outlet;
    a resilient valve element within an interior of the housing configured to control fluid flow through the inlet, the resilient valve element having a body comprising:
    a proximal portion forming a normally closed aperture configured to open when actuated by a medical device,
    a distal portion, and
    a central portion between the proximal portion and the distal portion, the central portion having a wall with an interior surface that defines a fluid chamber in the open mode and in the closed mode,
    the wall having a plurality of gland projections extending radially outwardly, at least one of the plurality of gland projections and the contact surface of the housing configured to maintain compressive contact to apply a radially inwardly compressive force on the resilient valve element when the valve is in the closed mode and thereby increase a stiffness of the wall to reduce waveform distortion as measured by the pressure transducer, the plurality of gland projections on the wall being spaced apart in a circular array around the central axis to form an interrupted ring, the interrupted ring forming interstices between gland projections, the wall having ribs, on an inner surface of the wall, that correspond to the interstices,
    at least one of the plurality of gland projections being distal of the normally closed aperture.

2. The medical valve of claim 1, wherein at least one of the plurality of gland projections contacts the contact surface when the valve is in the open mode.

3. The medical valve of claim 1, wherein the resilient valve element forms a lumen configured to receive a tip of the medical device.

4. The medical valve of claim 1, wherein at least one of the plurality of gland projections forms a ring around the wall.

5. The medical valve of claim 1, wherein the plurality of gland projections form a non-uniform ring around the wall.

6. The medical valve of claim 1, wherein the plurality of gland projections form a plurality of rings spaced apart with respect to the central axis of the resilient valve element.

7. The medical valve of claim 1, wherein at least one of the plurality of gland projections forms a slip plane with the resilient valve element.

8. The medical valve of claim 1, wherein the inlet and/or the outlet have at least one housing projection extending towards the central axis of the resilient valve element, the at least one housing projection configured to maintain compressive contact with the wall of the resilient valve element and to apply an inwardly compressive force on the resilient valve element when the valve is in the closed mode.

9. The medical valve of claim 8, wherein an interstice is formed between a pair of spaced apart gland projections, the housing projection being configured to contact the interstice.

10. The medical valve of claim 9, wherein the gland projections are spaced apart radially around the central axis.

11. The medical valve of claim 9, wherein the gland projections are spaced apart longitudinally.

12. The medical valve of claim 1, wherein the plurality of gland projections are disposed on the wall and spaced apart with respect to the central axis of the resilient valve element.

13. The medical valve of claim 1, wherein the compressive contact stiffens the wall of the resilient valve element and significantly reduces waveform distortion.

14. The medical valve of claim 1, wherein the compressive contact compresses a thickness of the wall of the resilient valve element by at least 1% when the valve is in the closed mode.

15. A method of reducing artifacts from a pressure-waveform reading taken from a pressure transducer that is in-line with a medical valve having an open mode that permits fluid flow, and a closed mode that prevents fluid flow, the method comprising:
   providing a pressure transducer in-line and in fluid communication with a valve, the valve comprising:
   a housing having an inlet and an outlet, the housing having an interior contact surface at and/or between the inlet and/or the outlet,
   a resilient valve element within the housing interior configured to control fluid flow through the inlet, the resilient valve element having a body comprising:
   a proximal portion having a normally closed aperture configured to open when actuated by a medical device,
   a distal portion adjacent to the outlet, and
   a central portion between the proximal portion and the distal portion, the central portion having a wall with an interior surface that defines a fluid chamber in the open mode and in the closed mode, the wall having at least one gland projection extending radially outwardly;
   compressively contacting the gland projection with the contact surface of the housing, when the valve is in the closed mode, to apply a radially inwardly compressive force on the resilient valve element, thereby increasing a stiffness of the wall; and
   displaying a reduced-artifact pressure waveform from the pressure transducer.

16. The medical valve of claim 15, wherein at least 180 degrees of a circumference of the resilient valve element has gland projections.

17. The method as defined by claim 15, wherein at least a portion of the gland projections are concyclic.

18. The method as defined by claim 15, wherein the gland projection extends along substantially the entire length of the central portion.

19. The method as defined by claim 15, wherein the gland projection extends radially along the surface of the wall.

20. A medical valve having an open mode that permits fluid flow, and a closed mode that prevents fluid flow, the medical valve comprising:
   a housing having an inlet and an outlet, the housing having an interior contact surface at and/or between the inlet and/or the outlet;
   a resilient valve element within the housing interior configured to control fluid flow through the inlet, the resilient valve element having a body comprising:
   a proximal portion forming a normally closed aperture configured to open when actuated by a medical device,
   a distal portion, and
   a central portion between the proximal portion and the distal portion, the central portion having a wall with an interior surface that defines a fluid chamber in the open mode and in the closed mode,
   means for compression extending radially outwardly from at least one or both of the central portion and the distal portion, the compression means and contact surface of the housing configured to maintain compressive contact to apply a radially inwardly compressive force on the resilient valve element when the valve is in the closed mode, thereby increasing a stiffness of the wall, the compression means being distal of the normally closed aperture, the compression means having at least two compression tabs that are connected by at least one compression tab strip.

21. The gland as defined by claim 20, wherein a plurality of the compression tabs connected by the compression tab strips form a non-uniform ring on the gland wall.

* * * * *